US006180606B1

(12) United States Patent
Chen et al.

(10) Patent No.: US 6,180,606 B1
(45) Date of Patent: *Jan. 30, 2001

(54) COMPOSITIONS WITH ENHANCED OSTEOGENIC POTENTIAL, METHODS FOR MAKING THE SAME AND USES THEREOF

(75) Inventors: Charles C. Chen, Potomac, MD (US); Steven R. Jefferies, York, PA (US)

(73) Assignee: GenSci Orthobiologics, Inc., Irvine, CA (US)

( * ) Notice: Under 35 U.S.C. 154(b), the term of this patent shall be extended for 0 days.

This patent is subject to a terminal disclaimer.

(21) Appl. No.: 09/006,583

(22) Filed: Jan. 13, 1998

Related U.S. Application Data

(63) Continuation-in-part of application No. 08/312,091, filed on Sep. 28, 1994, now Pat. No. 5,707,962, and a continuation-in-part of application No. 09/002,674, filed on Jan. 5, 1998.

(51) Int. Cl.[7] ............................... A61K 38/00; C07K 1/00
(52) U.S. Cl. ........................... 514/12; 514/21; 514/801; 424/85.1; 424/422; 424/423; 424/424; 530/351; 530/356; 530/399; 530/840; 128/DIG. 8
(58) Field of Search ................................ 514/12, 21, 801; 424/85–1, 422, 423; 530/351, 356, 399, 840; 128/DIG. 8

(56) References Cited

U.S. PATENT DOCUMENTS

| | | | |
|---|---|---|---|
| 2,516,438 | 7/1950 | Wheeler | 106/35 |
| 3,767,437 | 10/1973 | Cruz, Jr. | 106/161 |
| 4,172,128 | 10/1979 | Thiele et al. | 424/95 |
| 4,193,813 | 3/1980 | Chvapil | 106/122 |
| 4,209,434 | 6/1980 | Wilson et al. | 260/29.6 M |
| 4,291,013 | 9/1981 | Wahlig et al. | 424/16 |
| 4,294,753 | 10/1981 | Urist | 424/95 |
| 4,394,370 * | 7/1983 | Jefferies | 424/15 |
| 4,430,760 | 2/1984 | Smestad | 3/1.9 |
| 4,434,094 | 2/1984 | Seyedin et al. | 424/95 |
| 4,440,750 | 4/1984 | Glowacki et al. | 424/95 |
| 4,472,840 | 9/1984 | Jefferies | 3/1.9 |
| 4,485,097 | 11/1984 | Bell | 424/95 |
| 4,551,256 | 11/1985 | Urist | 424/95 |
| 4,563,350 | 1/1986 | Nathan et al. | 424/95 |
| 4,563,489 | 1/1986 | Urist | 524/21 |
| 4,596,574 | 6/1986 | Urist | 623/16 |
| 4,619,989 | 10/1986 | Urist | 530/417 |
| 4,620,327 | 11/1986 | Caplan et al. | 632/10 |
| 4,623,553 | 11/1986 | Ries et al. | 427/2 |
| 4,627,982 | 12/1986 | Seyedin et al. | 424/95 |
| 4,642,120 | 2/1987 | Nevo et al. | 623/16 |
| 4,678,470 | 7/1987 | Nashef et al. | 623/16 |
| 4,681,763 | 7/1987 | Nathanson et al. | 424/95 |
| 4,703,108 | 10/1987 | Silver et al. | 530/356 |
| 4,718,910 | 1/1988 | Draenert | 623/16 |
| 4,743,259 | 5/1988 | Bolander et al. | 623/16 |
| 4,789,732 | 12/1988 | Urist | 530/350 |
| 4,795,467 | 1/1989 | Piez et al. | 623/16 |
| 4,861,714 | 8/1989 | Denn, Jr. et al. | 435/684 |
| 4,975,526 | 12/1990 | Kuberasampath et al. | 530/350 |
| 5,001,169 | 3/1991 | Nathan et al. | 523/113 |
| 5,002,583 | 3/1991 | Pitaru et al. | 623/66 |
| 5,073,114 | 12/1991 | Detsch | 623/16 |
| 5,073,373 | 12/1991 | O'Leary et al. | 424/422 |
| 5,162,114 | 11/1992 | Kuberasampath et al. | 424/423 |
| 5,207,710 | 5/1993 | Chu et al. | 623/16 |
| 5,236,456 * | 8/1993 | O'Leary et al. | 623/16 |
| 5,264,214 | 11/1993 | Rhee et al. | 424/422 |
| 5,284,655 | 2/1994 | Bogdansky et al. | 424/422 |
| 5,290,558 | 3/1994 | O'Leary et al. | 424/422 |
| 5,531,791 | 7/1996 | Wolfinbarger, Jr. | 623/16 |
| 5,626,861 | 5/1997 | Laurencin et al. | 424/426 |
| 5,707,962 * | 1/1998 | Chen et al. | 514/12 |
| 5,766,618 | 6/1998 | Laurencin et al. | 424/426 |
| 5,866,155 | 2/1999 | Laurencin et al. | 424/425 |

FOREIGN PATENT DOCUMENTS

WO 89/04646 * 6/1989 (WO).
WO 96/39203 12/1996 (WO).

OTHER PUBLICATIONS

Bye, F. L. et al., "Histologic Evaluation of Periodontal Implants in a Biologically "Closed" Model" *Journal of Periodontology*, (Feb. 1987).

Connolly et al. "The Role of Bone Marrow in Osteogenesis" in Habal, M.B. et al., (eds.), Bone Grafts & Bone Substitutes, W.B. Saunders Company, Philadelphia 1992.

Cunningham et al.., "Biologic Principles of Bone Induction: Application to Bone Grafts" in Habal, M.B. et al., (eds.), Bone Grafts & Bone Substitutes, W.B. Saunders Company, Philadelphia 1992.

Donath et al., "A Histologic Evaluation of a Mandibular Cross Section One Year After Augmentation with Hydroxyapatite Particles" *Oral Surgery, Oral Medicine, Oral Pathology*, vol. 63, No. 6, pp. 651–655 (1987).

Glowacki, J., "Tissue Response to Bone–Derived Implants" in Habal, M.B. et al., (eds.), Bone Grafts & Bone Substitutes, W.B. Saunders Company, Philadephia 1992.

Mellonig, "Freeze–Dried Bone Allografts in Periodontal Reconstructive Surgery" *The Dental Clinics of North America: Reconstructive Periodontics*, vol. 35(3):505–520 (1991).

Pachence, J.M. "Collagen–Based Devices for Soft Tissue Repair" *J. of Biomat. Res.*, 33:35–40 (1996).

(List continued on next page.)

*Primary Examiner*—Christopher S. F. Low
*Assistant Examiner*—Abdel A. Mohamed
(74) *Attorney, Agent, or Firm*—Howrey Simon Arnold & White

(57) ABSTRACT

Osteogenic compositions, and methods for preparing same, which compositions comprise a porous or semi-porous matrix, an osteogenic factor and an agent such as growth factors, nutrient factors, drugs, calcium-containing compounds, blood products, large molecular weight proteins, or combinations thereof. These materials can be used in a wide range of clinical procedures to replace and restore osseous or periodontal defects.

56 Claims, No Drawings

OTHER PUBLICATIONS

Quteish and Dolby, "The Use of Irradiated–Crosslinked Human Collagen Membrane" *J. Clin. Periodontol.* 19:476–484 (1992).

Urist, M., "Bone Morphogenetic Protein" in Habal, M.B. et al., (eds.), Bone Grafts & Bone Substitutes, W.B. Saunders Company, Philadelphia 1992.

Wozney, J.M. and Rosen, V., "The BMP's In Bone Development And Repair" Portland Bone Symposium, Jun. 21–24 (1993).

Yamazaki et al., "Experimental Study on the Osteoindustion Ability of Calcium Phosphate Biomaterials with Added Bone Morphogenic Protein" *Transactions of the Society for Biomaterials*, p. 111 (1986).

* cited by examiner

COMPOSITIONS WITH ENHANCED OSTEOGENIC POTENTIAL, METHODS FOR MAKING THE SAME AND USES THEREOF

CROSS-REFERENCE TO RELATED APPLICATIONS

This application is a continuation-in-part of U.S. patent application Ser. No. 08/312,091, filed Sep. 28, 1994, now U.S. Pat. No. 5,707,962, and issued Jan. 13, 1998, and of the U.S. patent application Ser. No. 09/002,674 entitled "COMPOSITIONS WITH ENHANCED OSTEOGENIC POTENTIAL, METHODS FOR MAKING THE SAME AND THERAPEUTIC USES THEREOF" Jan. 5, 1998, in the name of Chen et al, each of which are fully incorporated by reference herein.

FIELD OF THE INVENTION

This invention is in the field of osteogenic bone repair compositions. More specifically this invention relates to bone repair compositions having enhanced osteogenic potential, to methods for making these bone repair compositions having enhanced osteogenic potential and to therapeutic uses for these compositions.

BACKGROUND OF THE INVENTION

A variety of methods and compositions of biomaterials have been used to repair or regenerate bone loss due to either trauma or disease. The term osteogenic commonly refers to substances which are osteoconductive and/or osteoinductive.

Conventional implantable bone repair materials provided a matrix or scaffolding for migration into, proliferation and subsequent differentiation of cells responsible for osteogenesis (Nashef U.S. Pat. No. 4,678,470). While the compositions provided by this approach provided a stable structure for invasive bone growth, they did not promote bone cell proliferation or bone regeneration. Generally, these materials are referred to as osteoconductive.

Subsequent approaches have used bone repair matrices containing bioactive proteins which when implanted into a bone defect provided not only a scaffolding for invasive bone ingrowth, but active induction of bone cell replication and differentiation. These materials are generally referred to as osteoinductive.

In general, osteoinductive compositions comprised a matrix which provided the scaffolding for invasive growth of the bone, anchorage dependent cells, and an osteoinductive protein source. The matrix may be a variety of materials, such as: collagen (Jefferies U.S. Pat. Nos. 4,394,370 and 4,472,840); inorganically based materials, such as a biodegradable porous ceramic (Urist U.S. Pat. No. 4,596,574); or, polylactic acid (Urist U.S. Pat. No. 4,563,489).

Osteogenic compositions and methods for making the same are described in Jefferies U.S. Pat. Nos. 4,394,370 and 4,472,840. Jefferies describes complexes of reconstituted collagen and demineralized bone particles or complexes of reconstituted collagen and a solubilized bone morphogenetic protein, fabricated into a sponge suitable for in vivo implantation into osseus defects. Structural durability of these compositions may be enhanced by crosslinking with glutaraldehyde.

In particular, two specific substances have a well established ability to induce the formation of new bone (i.e., to be osteoinductive) through the process of osteogenesis: demineralized bone particles or powder, and bone morphogenetic proteins (BMPs) (Urist U.S. Pat. Nos. 4,595,574, 4,563,489, 4,551,256). A variety of other bone inducing factors have been characterized as well (Seydin et al., U.S. Pat. No. 4,627,982).

While a wide variety of osteoinductive compositions have been used in bone repair and regeneration there is always need in the art for improvements or enhancements of existing technologies which would accelerate and enhance bone repair and regeneration allowing for a faster recovery for the patient receiving the osteogenic implants.

SUMMARY OF THE INVENTION

This invention relates to bone repair compositions having enhanced osteogenic potential. Osteogenic bone repair compositions in accordance with this invention are used as implants, to repair, form, or regenerate bone in the treatment of osseous or periodontal defects. An osseous or periodontal defect is an osseous or periodontal location, respectively, where generation of osseous tissue is therapeutically beneficial or cosmetically desired.

Osteogenic compositions in accordance with the invention can comprise a porous or semi-porous matrix and at least one osteogenic factor, wherein one or more growth factors, drugs, nutrients, antimicrobial agents, blood proteins or products, or calcium containing compounds are on or within the matrix of the osteogenic composition, and/or on or within the osteoinductive factor of the composition. The osteogenic bone repair material of this invention, produced by the methods described herein, exhibit enhanced osteogenic potential relative to known osteogenic bone repair compositions used as implants to repair bone defects.

It is a general object of this invention to provide improved osteogenic compositions comprising a porous or semi-porous matrix and at least one osteogenic factor.

It is a more specific object of this invention to provide an improved osteogenic composition comprising a porous or semi-porous collagen matrix and either demineralized bone particles or Bone Morphogenetic Proteins, or proteins, and the growth factor TGF-$\beta$2.

It is a further object of this invention to provide improved osteogenic compositions comprising a porous or semi-porous matrix, at least one osteogenic factor, and at least one nutrient factor.

It is yet another object of this invention to provide improved osteogenic compositions comprising a porous or semi-porous matrix, at least one osteogenic factor, and at least one drug.

It is yet another object of this invention to provide improved osteogenic compositions comprising a porous or semi-porous matrix, at least one osteogenic factor, wherein at least one antimicrobial, blood protein or product, or calcium containing compound is present on or within the matrix, and/or on or within the osteoinductive factor.

It is a further object of this invention to provide methods of making the improved osteogenic compositions.

It is yet a further object of this to provide methods of use for these improved osteogenic compositions in the repair of osseous or periodontal defects.

Further objects and advantages of the present invention will become apparent from the description that follows.

DETAILED DESCRIPTION OF THE INVENTION

The present invention relates to osteogenic compositions having enhanced osteogenic potential. Thus, the invention relates to osteogenic compositions having enhanced osteogenic potential which comprise a porous or semi-porous matrix, at least one osteoinductive factor, and a growth factor, nutrient factor, drug, calcium containing compound, antimicrobial agent, blood protein or products, or combinations thereof.

The osteogenic compositions in accordance with the invention can comprise a porous or semi-porous matrix and at least one osteoinductive factor, wherein at least one growth factor is present on or within the matrix, and/or on or within the osteoinductive factor. Thus, the osteoinductive factor can be the growth factor, whereby the composition has two components, a matrix and an osteoinductive growth factor.

Alternatively, osteogenic compositions in accordance with the invention can comprise a porous or semi-porous matrix, at least one osteoinductive factor, wherein at least one nutrient factor is present on or within the matrix, and/or on or within the osteoinductive factor. Thus, the matrix can be the nutrient factor, whereby the composition has two components, a matrix and an osteoinductive factor.

Preferred embodiments of the compositions in accordance with the invention were determined based on an observation that specific combinations of osteoinductive factors and growth factors have a synergistic effect in enhancing bone repair. Alternative preferred embodiments of the invention comprise osteogenic compositions which comprise various combinations of a matrix; osteoinductive factor(s); and, nutrient factors, drugs, antimicrobial agents, calcium containing compounds, blood proteins or products or other agents which result in enhanced hard tissue healing or bone repair.

A Porous or Semi-Porous Matrix

Compositions comprising a porous or semi-porous matrix and one or more osteoinductive elements are comprised of materials known in the art and prepared by known methods. The growth factors, nutrient factors, or other agents may be present within or on the matrix or reside in a matrix void. When an agent is comprised by the matrix, it is covalently attached to the matrix, or is encompassed by the matrix void space; in these situations, the agent will generally be referred to as within the matrix.

The matrix may comprise organic materials; inorganic materials, such as ceramics; or, synthetic polymers. Examples of organic materials that can be used to form the matrix include, but are not limited to, collagen, polyamino acids, or gelatin. The collagen source maybe allogeneic, or xenogeneic relative to the mammal receiving the implants. The collagen may also be in the form atelopeptide or telopeptide collagen. Examples of synthetic polymers that can be used to form the matrix include, but are not limited to, polylactic acids, polyglycolic acids, or combinations of polylactic/polyglycolic acids. Resorbable polymers, as well as non-resorbable polymers may constitute the matrix material. The presently preferred density of the matrix is between 0.010 and 0.05, and most preferably between 0.07 and 0.045 grams/cubic centimeter or greater. Matrixes having this density are believed to exhibit enhanced pore structure stability when growth or nutrient factors or other agents are within or on the matrix.

One of skill in the art will appreciate that the terms porous or semi-porous refer to the varying density of the pores in the matrix. One of skill in the art will also appreciate that inorganic fillers or particles, such as hydroxyapatite, tri-calcium phosphate, ceramic glasses such as Bioglass, amorphous calcium phosphates, porous ceramic particles or powders, mesh or particulate titanium or titanium alloy may also be added to a matrix. Mineralized or partially mineralized freeze-dried, particulate bone may also be used for this purpose.

A preferred method for producing the collagen to be used, is performed by dispersing natural insoluble collagen in an acid or alkaline solution, homogenizing the dispersion in a WARING® Blender under cold [4° Centigrade (C.)] conditions. One of skill on the art will understand that the collagen dispersion may be treated with the enzyme Ficin to remove non-collagen proteins and cellular material, and/or may be treated with other proteolytic enzymes, such as pepsin or trypsin, to remove telopeptide regions of the collagen macromolecule, thus potentially reducing antigenicity especially when a non-allogeneic natural tissue source is used to extract the collagen. Hypertonic salt may be added to the collagen dispersion to effect precipitation of the solubilized collagen, or the acid dispersion is dialyzed against saline at physiologic pH 7.4 to promote fibrillogenesis. The precipitate can be spun down in a medium-to-high speed ultracentrifuge and resuspended in a dilute acid or base solution to effect resolubilization.

By way of example, the optimal pH ranges for the solubilized or dispersed collagen suspensions are anywhere from about pH 1.5 to 5.5 in the acid range and from about pH 8.0 to 12.0 in the alkaline range.

The source of the collagen may be from human or animal sources, or could be in a recombinant form expressed from a cell line, or bacteria. Human sources are presently preferred. Once the collagen has been extracted from the tissue, the purified collagen may either be in the form of an aqueous acidic or basic dispersion, or alternatively, as a lyophilized dry powder or fleece as an acidic or basic collagen salt.

Osteoinductive Factors

Examples of osteoinductive factors that may be complexed with the matrix include, but are not limited to demineralized bone particles, Bone Morphogenetic Proteins (BMP), such as BMP-2 and BMP-7, and other osteoinductive factors such as extracts of demineralized bone matrix. Although demineralized bone powder is preferred, one or more purified or partially purified Bone Morphogenetic Proteins (BMPs), preferably BMP-2 or BMP-7, or combinations thereof can be used with or instead of particulate demineralized bone powder (Jefferies U.S. Pat. Nos. 4,394, 370 and 4,472,840). A weight of BMP ranging from the micrograms to milligrams of BMP per milligram of collagen may be used. By way of example, 100 micrograms of BMP per milligram collagen may be used.

Examples of other BMPs which can be placed with the matrix by conventional methods include, but are not limited to, BMP-2a, BMP-4, BMP-5, BMP-6, BMP-8 (Wozney, J. M. and Rosen V: "The BMP's In Bone Development And Repair," Portland Bone Symposium, Jun. 21–24, 1993).

The use of the term demineralized bone particle herein is intended to encompass bone particles of a wide range of sizes, including bone powders, fragments or chips.

Osteoinductive factors can include "extracted demineralized bone particles" to which an osteogenic compound or composition has been absorbed. Generally, extracted demineralized bone matrix particles are treated with a chaotropic agent to remove as much non-collagen proteins and immunologic elements as possible, thereby creating a "type 1 collagen particle." Alternatively, the demineralized bone powder can be selectively remineralized to facilitate osteogenesis. (See e.g., PCT International Publication Number WO/9639203, published Dec. 12, 1996, in the name of Biocoll Laboratories, Inc.)

By way of example, the osteogenic composition may comprise collagen as the porous or semi-porous matrix and demineralized bone particles as the osteoinductive factor.

Demineralized bone particles or powder, or Bone Morphogenetic Protein or proteins, such as BMP-2, BMP-2a, or BMP-7, can be blended with a collagen matrix by conventional methods, such as a powder blend, as a hydrated or liquid form added to the dry collagen powder or fleece, as a dry lyophilized powder into an aqueous collagen dispersion, or as a hydrated or liquid form of the demineralized bone powder or of the Bone Morphogenetic Protein or Proteins. For example, specific methods of combining reconstituted collagen with demineralized bone particles and/or bone morphogenetic protein are described by Jefferies in U.S. Pat. Nos. 4,394,370 and 4,472,840.

The collagen/demineralized bone osteogenic composition described above can be produced in the form of a dehydrated sponge, powder, particles, membrane, fleece or fibers by standard methods known to one of skill in the art. A collagen/demineralized bone sponge may be ground into particles, powder or fleece by conventional methods. The weight ratio of the collagen to demineralized bone particles may be similar to that described in Jefferies et al., U.S. Pat. No. 4,394,370. Alternatively, the weight ratio may range from 10% to 90% collagen and 90% to 10% demineralized bone particles.

Growth Factors

In preferred embodiments, this invention relates to osteogenic compositions comprising a porous or semi-porous matrix and at least one osteoinductive factor, wherein one or more growth or nutrient factors are present within or on the matrix complexed with the osteoinductive factor.

Thus, cytokines and prostaglandins may be present within or on the porous or semi-porous matrix which has been, or will be complexed with an osteoinductive factor or factors, and/or cytokines or prostaglandins are present on or within the osteoinductive factor or factors. For example, a growth factor used in compositions of the invention may be of natural origin or recombinantly or otherwise produced by conventional methods. Such growth factors are also commercially available. Combinations of two or more growth factors may be applied to the osteogenic compositions to further enhance osteogenic or biologic activity of the implants.

Examples of growth factors that may be used on or within the porous or semi-porous matrix, and/or on or within the osteoinductive factor, include, but are not limited to: Transforming Growth Factor-Beta (TGF-$\beta$), such as TGF-$\beta$1, TGF-$\beta$2, and TGF-$\beta$3; Transforming Growth Factor-Alpha (TGF-$\alpha$); Epidermal Growth Factor (EGF); Insulin Like Growth Factor-I or II; Interleukin-I (IL-I); Interferon; Tumor Necrosis Factor; Fibroblast Growth Factor (FGF); Platelet Derived Growth Factor (PDGF); Nerve Growth Factor (NGF); and, molecules that exhibit growth factor or growth factor-like effects.

One embodiment of the invention, for use as an implant, comprises a matrix of collagen complexed with demineralized bone particles, BMP, BMPs or combinations thereof to which is added one or more soluble growth factors. The growth factors may be within the matrix or, e.g., be sorbed onto the matrix in an aqueous or other solution liquid. The collagen matrix complexed with the osteoinductive factor to which the soluble growth factor is to be added, may be in the form of a semi-porous or porous sponge, (Jefferies U.S. Pat. Nos. 4,394,370 and 4,472,840) a membrane, a fiber-like structure, powder, fleece, particles or fibers. (See, e.g., J. M. Pachence, "Collagen-Based Devices for Soft Tissue Repair", *J. Biomat. Res.* 33:35–40 (1996)).

The growth factor or factors may be delivered to the collagen demineralized bone compositions in a liquid form, but can be provided in a dry state prior to reconstitution and administration onto or into the collagen-demineralized bone or BMP compositions. One of skill in the art will appreciate that the growth factor present on or within the matrix may reside within the void volume of the porous or semi-porous matrix.

By way of example, the growth factor TGF-$\beta$ can be present on or within the collagen matrix of the collagen demineralized bone osteogenic composition which has the form of a sponge. Preferably, the growth factor TGF-$\beta$2 is used. The TGF-$\beta$2 may be natural or synthetic in origin. The TGF-$\beta$2 is contacted with the sponge allowing the growth factor to be located on or within the matrix and void volume of the porous or semi-porous structure of the sponge. Alternatively, the TGF-$\beta$2 is contacted with the osteogenic factor allowing the growth factor to be located on or within the osteogenic factor. The amount of the TGF-$\beta$2 added to the sponge and/or osteogenic factor can range from nanogram to milligram quantities. A preferred amount of TGF-$\beta$2 to be added is about 0.1 ng to 500 mg, more preferred is about 10 ng to 100 mg, and most preferable is about 100 ng to 5 mg per 40 to 80 mg of sponge. By way of example, a collagen-demineralized bone osteogenic sponge comprising 75% collagen and 25% demineralized bone powder (weight ratio), may have added on or within the matrix and/or osteoginductive factor, about 5 $\mu$g of TGF-$\beta$2 per 40 mg of sponge or per 80 mg of sponge.

Nutrient Factors and Other Agents

In addition to growth factors, nutrient factors, drugs, calcium-containing compounds, anti-inflammatory agents, antimicrobial agents, blood products, large molecular weight proteins, glycoproteins, carbohydrates, cell culture medias, and additional Bone Morphogenetic Factor (or Factors), or combinations thereof, may be on or within the matrix and/or osteoinductive factor of a composition in accordance with the invention. For example, these agents can be added via sorption of a liquid fraction containing such agent(s).

Examples of nutrient factors that can be used in accordance with the present invention include, but are not limited to, vitamins, hormones, individual or combinations of amino acids, carbohydrates or derivatives thereof, fats or derivatives thereof, alcohols or derivatives thereof, inorganic salts, and trace elements. For example, the nutrient factor can be glycerol or collagen.

Examples of drugs that can be used in accordance with the invention, include, but are not limited to, tetracycline or antimicrobial agents such as chlorahexadine or zinc citrate. Suggested amounts for a drug, are 0.1:1 wt drug/wt collagen ratios. Examples of drugs that may be used in accordance with the invention include, but are not limited to, anti-inflammatory agents such as steroidal or nonsteroidal agents. One presently preferred non-steroidal agent is flurbiprofen. As appreciated by one of ordinary skill in the art, any drug which will have a therapeutic, remedial or cosmetic benefit can be used in accordance with the invention.

In yet another embodiment, blood products such as fibrin, fibronectin, or blood clotting factors can be used in accordance with the invention.

In another embodiment, calcium containing compounds such as calcium hydroxide, calcium lactate and inorganic or organic calcium salts can be used in accordance with the invention.

In another embodiment, large molecular weight proteins, such as enzymes; or extracellular matrix proteins, such as laminin or fibronectin, may be used in accordance with the invention.

The drugs, calcium containing compounds, blood products, or large molecular weight proteins, may be located within or on the semi-porous or porous matrix, and in certain embodiments are sorbed onto or into the matrix.

Methods of Preparing Compositions in Accordance With the Invention

The present invention comprises a method of making an osteogenic implant having enhanced osteogenic potential. A method in accordance with the invention comprises steps of obtaining a porous or semi-porous matrix, combining the matrix with at least one osteoinductive factor; and adding into or onto said porous or semi-porous matrix and/or said osteoinductive factor, at least one agent such as growth factors, nutrient factors, drugs, antimicrobial agents, calcium-containing compounds, blood proteins or products, anti-inflammatory agents, large molecular weight proteins, or any combination thereof. For example, the osteogenic composition can be dehydrated and subsequently rehydrated in the active factor solution in a sorbing step.

The osteogenic composition may be chemically crosslinked with agents known in the art (e.g., glutaraldehyde).

These compositions can be used therapeutically, e.g., as a grafting implant in orthopedic, plastic, or reconstructive surgery, in periodontal procedures, and in endodontic procedures and are implanted by standard surgical or dental procedures. The osteogenic implants of this invention having enhanced osteogenic potential are suitable for both human and veterinary use.

The following examples are by way of illustrative aspects of the invention but are in no way intended to limit the scope thereof.

EXAMPLES

Example 1

A collagen-demineralized bone conjugate was fabricated from sponges derived from tendon collagen combined with human, freeze-dried, demineralized bone particles. The collagen source can be human or animal, such as bovine, porcine, equine or ovine.

To prepare a sponge from human collagen, human tendon obtained from cadavers at an organ bank was cut into thin slices, preferably 1 to 3 mm in thickness. These tendon slices were washed in 1 M NaCl or some other suitable hypertonic salt solution. Optionally one may substitute a solution of NaOH in a concentration range of from 0.001 to 2 molar (normal), optionally adding NaCl, to assist in the removal of debris and contaminating substances.

The tendon slices were removed from the initial washing/decontamination solution and replaced in a washing solution of sterile water with frequent contacts to remove the initial washing solution. The tendon slices were washed with numerous contacts of fresh sterile water anywhere from two to ten times.

The tendon slices were then transferred to a metal basket with a perforated bottom and immersed in a one (1) liter beaker filled with approximately 540 ml of phosphate buffer and 540 mg of FICIN (Sigma Chemical Co., St. Louis, Mo.). The FICIN activity ranged from about 0.25 to 0.75 units per milligram FICIN;. a unit is defined as the amount of FICIN which will produce a $\Delta$ A280 of 0.1 per minute at pH 7.0 at 37° C., when measuring TCA soluble products from casein in a final volume of 1.0 ml (1 centimeter (cm) light path). The tendon slices were subjected to mild agitation in the phosphate buffer-FICIN bath or 30 to 60 minutes at room temperature (20° to 28° C.).

Preferably, the tendon slices were washed with several changes of distilled water prior to addition of the dilute (0.01 N) HCl. The tendon slices were immersed in the 0.01 N HCl solution for at least 24 hours at 4° C. At the end of this contact time, the tendon slices in the 0.01 N HCl were transferred to a sterile WARING® Blender. The blender was activated in short 15 to 30 second intervals in order to disperse the tendon material into a slurry dispersion. The dispersion and blender vessel were maintained on ice, to keep the temperature close to 4° C., to dissipate the heat generated by the blender and the blending procedure. The dispersed tendon slurry was then, optionally, passed through a 50 to 1000 micron filter (using vacuum) to remove any tendon particles that were not completely dispersed.

The tendon dispersion (optionally filtered) was precipitated and concentrated by the addition of 1 M NaCl, and collected on a sterile glass rod. The collected tendon collagen fiber precipitate was redispersed in a cold solution of sterile water containing approximately a concentration of 0.01 N HCl (50 ml of 0.01 N HCl per gram of wet weight precipitated collagen material). The precipitate was covered and refrigerated at 2° to 8° C. for 16 to 24 hours.

The precipitated collagen material in acid solution was dispersed in a sterile WARING® Blender using short bursts at low speed. The dispersed tendon collagen was then dialyzed against multiple changes (2 to 10 times) of sterile distilled water (3× to 10× volume).

The dialyzed tendon collagen dispersion was then freeze-dried (lyophilized) by first freezing the dispersion in labeled trays in a freeze-drier. The collagen was held for 16 to 24 hours at −40 degrees C., the temperature is then raised to −8 degrees C. and vacuum was initiated. Vacuum was applied for a sufficient time period (approximately 24 to 72 hours) to lyophilize the tendon collagen dispersion. Those skilled in the art will recognize that the wide range of cooling and vacuum cycles may be appropriate to arrive at a satisfactory lyophilized end-product. The resultant sponge-like material was then shredded into a powder using a WARING® Blender. The powdered lyophilized sponge material was stored under sterile conditions until needed for blending into composite osteogenic compositions.

The lyophilized tendon collagen fleece or powder was weighed; this weight was considered to be the dry weight of the material. The tendon powder (dry weight) was proportioned with a portion of dry demineralized bone particles and blended until a uniform dry powder blend was achieved.

The weight ratio of collagen to demineralized bone particles may be similar to that described in Jefferies U.S. Pat. No. 4,394,370. Alternatively, the weight ratio of the tendon collagen powder or fleece to demineralized bone powder can range anywhere from about 90% tendon collagen with 10% demineralized bone powder or particles, to about 10% collagen with 90% demineralized bone particles.

The powder blends are stored under sterile conditions until needed for reconstitution and, e.g., lyophilization into an osteogenic sponge form.

Example 2

To prepare extracted demineralized bone particles which can serve as a matrix component of a composition in accordance with the invention, extracted demineralized bone matrix particles are treated with a chaotropic agent to remove as much non-collagen proteins and immunologic elements as possible, thereby creating a "type 1 collagen particle." Such particles are used to deliver osteoinductive molecules or factors.

An extraction procedure to prepare such particles comprises: immersing a suitable quantity of demineralized bone matrix particles in a chaotropic agent, e.g., guanidinium hydrochloride buffered with 50 millimolar phosphate buffer at pH 7.4. The particles are maintained in this extraction medium at 4 degrees C. for 10 to 20 hours with mild agitation. Optionally, protease inhibitors such as 0.5 millimolar phenyl methyl-sulfonyl fluoride and/or 0.1 molar 6-aminohexanolic acid were added to the extraction medium. At the end of the extraction period, the extracted demineralized bone matrix particles were removed from the extraction solution by vacuum filtration, or by centrifugation at 800 to 1000 rpm. The extracted demineralized freeze dried bone allograft particles (EDFDBA) were washed 10 to 30 times in sterile phosphate buffered saline. The particles were then dialyzed against several changes of neutral phosphate buffered saline to remove any remaining chaotropic agent. The particles were then placed in an appropriate inorganic or organic acid or base; an organic solvent such as ethanol, isopropanol, or acetone; or a buffer such as phosphate buffered saline to facilitate swelling of the particles.

The appropriate bioactive/osteoinductive agent may be added to the initial swelling medium, or alternatively added to the particles in appropriate buffer after contact with the swelling medium. After an appropriate contact time with the bioactive/osteoinductive agent, the complexed particles were separated by vacuum filtration, and either used in a dry or wet state for incorporation into the porous or semi-porous implant.

Example 3

In this example, pulverized tendon collagen powder or fleece prepared in accordance with Example 1, was blended with demineralized bone particles at a weight ratio of 0.66 grams of demineralized bone powder for each gram of dry tendon collagen. For each gram of collagen material in the blended mixture, 50 mls of a solution of sterile water with 4.7% ethanol was added to the powder blend and mixed to form a thick aqueous dispersion. The mixture was then blended in a WARING® Blender with short burst of 5 to 10 seconds on slow speed until uniformly dispersed in an aqueous slurry.

The collagen bone powder mixture was then poured into anodized aluminum trays and placed in a lyophilizer. The composite tendon collagen-demineralized bone dispersion was first frozen for 10 hours at minus 40° C., then the automatic cycle was initiated to begin the lyophilization. The composite sponge was lyophilized in an automated cycle over a 50 hour period, with the lower unit temperature below −40° C. and the upper chamber between 2° and 8° C. When the lyophilization was complete, the intact sponge was removed, cut into desired size pieces, placed in an appropriate package configuration, and then sterilized by E-Beam or Gamma radiation methods. Alternatively, the intact sponge was pulverized into a fleece powder, or particles using a WARING® Blender and dry blending, or using an appropriate dry powder mill.

To prepare a composition in the form of a membrane, the composite tendon collagen-demineralized bone dispersion was not lyophilized, but rather poured into an appropriately sized sterile tray or dish, placed in a sterile area or laminar flow box, and allowed to dehydrate into a cast collagen membrane. Optionally, the membrane was crosslinked by elevated thermal storage, by UV radiation, or by chemical means such as immersion in a glutaraldehyde solution at concentrations from about 0.005% to 1.0%.

Example 4

A collagen composite sponge was prepared as described in Example 3, but a bovine tendon collagen was used as the collagen source. The weight ratio of bovine collagen to demineralized bone powder was about 75% collagen to 25% demineralized bone. Alternatively, the bovine collagen source used may be from hide, instead of tendon. This hide collagen is prepared by conventional methods in accordance with the present disclosure.

Example 5

An osteogenic collagen sponge was fabricated as described in Example 3, but a lyophilized Bone Morphogenetic Protein (RMP) was blended with the pulverized tendon collagen particles instead of demineralized bone. A weight ratio of BMP from the micrograms to milligrams of BMP to mg collagen may be used. In this specific example, 100 micrograms BMP per milligram collagen was blended then dispersed in aqueous solution, prior to lyophilization into a sponge configuration as described in Example 2. The BMP was extracted from bone by conventional methods (Jefferies U.S. Pat. Nos. 4,394,370 and 4,472,840, and Urist U.S. Pat. No. 4,455,256). This collagen-BMP composite may be cast into a membrane, e.g., as described in Example 1, or the composite in a sponge configuration may be ground into a powder or fleece.

Example 6

A growth factor, in aqueous or liquid form, was sorbed in and/or onto the porous structure of a composite osteogenic sponge in the following manner: A collagen-demineralized bone particle sponge was removed from its sterile package and placed in a sterile plastic disposable dish.

Approximately 5 micrograms ($\mu$g) of Transforming Growth Factor Beta-2 (Celltrex, Palo Alto, Calif.) was reconstituted in sterile saline, and applied with a sterile syringe or pipette to the osteogenic composite sponge. After about 1 to 10 minutes, the sponge with the growth factor sorbed thereto was applied to an appropriate osseous defect, in accordance with standard protocols clinical protocols. The weight of growth factor applied to a 75–80 mg sponge can range from nanograms to milligram amounts of growth factor in aqueous or liquid form.

Example 7

As an alternative to the addition of growth factor(s) set forth in Example 6, the growth factor or factors are applied to a pulverized sponge which, therefore, has a powder or fleece form. For example, 5 micrograms of Transforming Growth Factor Beta-2, in sterile saline or physiologic buffer, was added to the composite powder in a sterile vial, lightly agitated, allowed to stand for 1 to 10 minutes. The hydrated osteogenic powder was then applied to an osseous defect requiring treatment.

Example 8

As a further example of the addition of growth factor(s) such as set forth in Examples 6 and 7, the growth factor or factors were applied to an osteogenic composition in accordance with the invention which is in the form of a membrane, as described in Example 3. For example, a collagen-demineralized bone membrane consisting of 5 to 10% demineralized bone particles and 90 to 95% collagen material were rehydrated in a growth factor solution prior to implantation on and/or into an osseous defect.

Alternatively, the membrane may be used as a barrier membrane in a guided tissue regeneration procedure over a periodontal or alveolar defect. (See, e.g., Quteish and Dolby, "The Use of Irrradiated-Crosslinked Human Collagen Membrane" *J. Clin. Periodontal.* 19:476–484 (1992)).

Example 9

In accordance with the method set forth in Example 9, growth factors are attached to the surface of extracted demineralized bone matrix particles. Thereafter, in accordance with the present disclosure, the particles are added to the matrix to form a composition.

For example, the method in accordance with Example 9 can be carried out with several growth factors. The resulting extracted demineralized bone matrix particles having the various growth factors attached thereto are then added to a matrix. The various particles can be mixed and then added to the matrix, or applied to the matrix in sequence or in any combination thereof as appreciated by one of skill in the art. Accordingly, this method provides for the incorporation of multiple growth factors with different diffusion-controlled patterns of release or availability together with the osteoinductive factor or element in the implant. Diffusion-controlled patterns of release or availability are inherent properties of individual growth factors, and are also affected by the location of the implant.

Example 10

In embodiments of compositions in accordance with the invention that comprise a matrix, an osteoinductive factor and a separate growth factor, the order of application or spatial location of the growth factors and osteoinductive element can be altered. For example, the growth factors can be sorbed onto the surface of the matrix, then the osteoinductive factor added as a solution which is sorbed onto or into the porous or semi-porous matrix. Alternatively, the growth factors can be sorbed onto the extracted demineralized bone particles, and then the osteoinductive factor and particle mixture added as a solution which is sorbed onto or into the matrix.

CLOSING

While the invention has been described with reference to certain specific embodiments, it will be appreciated that many more defections and changes may be made by those skilled in the art without departing from the spirit of the invention.

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar to equivalent to those described herein can be used in the practice or testing of the invention, the preferred methods and materials are now described. All publications mentioned herein are fully incorporated herein by reference.

We claim:

1. An osteogenic composition having enhanced osteogenic potential, the composition comprising
    a porous or semi-porous matrix;
    at least one osteoinductive factor; and,
    at least one growth factor, nutrient factor, drug, calcium-containing compound, anti-inflammatory agent, antimicrobial agent, blood product, large molecular weight protein, or combination thereof present on or within the porous or semi-porous matrix or present on or within the osteoinductive factor.

2. The composition of claim 1, wherein the porous or semi-porous matrix is resorbable or non-resorbable.

3. The composition of claim 1, wherein the porous or semi-porous matrix comprises a form of a sponge, a membrane, a fibrous structure, a powder, a fleece, or particles.

4. The composition of claim 1, wherein the at least one osteoinductive factor comprises mineralized, partially mineralized or remineralized bone.

5. The composition of claim 1, wherein the at least one osteoinductive factor is particulate.

6. The composition of claim 1, wherein the at least one osteoinductive factor is freeze-dried.

7. The composition of claim 1, comprising a growth factor, which comprises a cytokine or a prostaglandin.

8. The composition of claim 1, wherein the growth factor is of natural origin or is recombinantly produced.

9. The composition of claim 1, comprising a combination of two or more growth factors.

10. The composition of claim 1, wherein the at least one osteoinductive factor is the at least one growth factor.

11. The composition of claim 1, wherein the matrix comprises collagen and the osteoinductive factor comprises demineralized bone particles, and wherein weight ratio of demineralized bone particles to collagen is 10% to 90% collagen, to 90% to 10% demineralized bone particles.

12. The composition of claim 1, further comprising a glycoprotein, carbohydrate, cell culture media, a Bone Morphogenetic Factor, or combination of Bone Morphogenetic Factors.

13. The composition of claim 1, wherein the matrix comprises human collagen and the osteoinductive factor comprises demineralized bone particles, and wherein the weight percent ratio of human collagen to demineralized bone particles is in a range of about 60% human collagen to 40% demineralized bone particles, to 10% human collagen to 90% demineralized bone particles.

14. The composition of claim 1 comprising a nutrient factor, wherein the nutrient factor is a vitamin, hormone, individual or combination of amino acids, carbohydrate or derivative thereof, fat or derivative thereof, alcohol or derivative thereof, inorganic salt, or trace element.

15. The composition of claim 1 comprising a nutrient factor, wherein the nutrient factor is glycerol.

16. The composition of claim 1 comprising a drug, wherein a weight ratio of the drug to the matrix is about 0.1 weight percent drug to 1 weight percent matrix.

17. The composition of claim 1, comprising a blood product, wherein the blood product is fibrin, fibronectin, or a blood clotting factor.

18. The composition of claim 1 comprising a calcium-containing compound, wherein the calcium-containing compound is calcium hydroxide, calcium lactate, an inorganic calcium salt, or an organic calcium salt.

19. The composition of claim 1, wherein the nutrient factor is collagen.

20. The composition of claim 1, further comprising inorganic fillers or particles.

21. The composition of claim 20, where the inorganic fillers or particles are hydroxyapatite, tri-calcium phosphate, ceramic glass, amorphous calcium phosphate, porous ceramic particles or powders, mesh titanium or titanium alloy, or particulate titanium or titanium alloy.

22. The composition of claim 1, wherein the osteoinductive factor comprises demineralized bone particles, a Bone Morphogenetic Protein, an osteoinductive extract of demineralized bone matrix, or a combination thereof.

23. The composition of claim 22, wherein the osteoinductive factor comprises a Bone Morphogenetic Protein which is Bone Morphogenetic Protein-2 (BMP-2), Bone Morphogenetic Protein-2a (BMP-2a), Bone Morphogenetic Protein-4 (BMP-4), Bone Morphogenetic Protein-5 (BMP-5), Bone Morphogenetic Protein-6 (BMP-6), Bone Morphogenetic Protein-7 (BMP-7), or Bone Morphogenetic Protein-8 (BMP-8).

24. The composition of claim 1, comprising a growth factor wherein the growth factor is selected from the group consisting of: Transforming Growth Factor-Beta (TGF-β), Transforming Growth Factor-Alpha (TGF-α), Epidermal Growth Factor (EGF), Insulin Like Growth Factor-I or II, Interleukin-I (IL-I), Interferon, Tumor Necrosis Factor, Fibroblast Growth Factor (FGF), Platelet Derived Growth Factor (PDGF), and Nerve Growth Factor (NGF).

25. The composition of claim 24, wherein the growth factor is Transforming Growth Factor-Beta (TGF-β), which is Transforming Growth Factor-Beta-1 (TGF-β1), Transforming Growth Factor-Beta-2 (TGF-β2), or Transforming Growth Factor-Beta-3 (TGF-β3).

26. The composition of claim 1, wherein the porous or semi-porous matrix comprises the at least one growth factor, nutrient factor, drug, calcium-containing compound, anti-inflammatory agent, antimicrobial agent, blood product, large molecular weight protein, or combination thereof.

27. The composition of claim 26, wherein the porous or semi-porous matrix is at least one nutrient factor.

28. The composition of claim 1 comprising a drug, wherein the drug is tetracycline or an antimicrobial agent.

29. The composition of claim 28 comprising an antimicrobial agent, wherein the antimicrobial agent is chlorahexadine or zinc citrate.

30. The composition of claim 1 comprising an anti-inflammatory agent, wherein the anti-inflammatory agent is a steroidal agent or a nonsteroidal agent.

31. The composition of claim 30 comprising a nonsteroidal anti-inflammatory agent, where the nonsteroidal anti-inflammatory agent is flurbiprofen.

32. The composition of claim 1 comprising a large molecular weight protein, wherein the large molecular weight protein is an enzyme or extracellular matrix protein.

33. The composition of claim 32 wherein the large molecular weight protein is an extracellular matrix protein which is laminin or fibronectin.

34. The composition of claim 1, wherein the porous or semi-porous matrix is an organic material or an inorganic material.

35. The composition of claim 34, wherein the porous or semi-porous matrix comprises a ceramic or a synthetic polymer.

36. The composition of claim 35, wherein the porous or semi-porous matrix comprises a synthetic polymer which comprises polylactic acids, polyglycolic acids, or combinations of polylactic and polyglycolic acids.

37. The composition of claim 34, wherein the porous or semi-porous matrix comprises an organic material which is polyamino acids, gelatin, or collagen.

38. The composition of claim 37, wherein the porous or semi-porous matrix comprises collagen which is allogeneic or xenogeneic.

39. The composition of claim 37, wherein the porous or semi-porous matrix comprises collagen which is atelopeptide or telopeptide collagen.

40. The composition of claim 37, wherein the porous or semi-porous matrix comprises collagen, and wherein the collagen is human, bovine, equine, porcine or ovine collagen.

41. The composition of claim 40 wherein the collagen is bovine, and wherein the weight percent ratio of bovine collagen to demineralized bone particles is in a range of about 75% bovine collagen to about 25% demineralized bone particles.

42. The composition of claim 40 wherein the matrix comprises human collagen and the osteoinductive factor comprises Bone Morphogenetic Protein, and wherein the weight percent ratio of human collagen to Bone Morphogenetic Protein is in a range of about 1 weight unit Bone Morphogenetic Protein to 1 weight unit human collagen, to 1 weight unit Bone Morphogenetic Protein to 1000 weight units human collagen.

43. An osteogenic composition having enhanced osteogenic potential, the composition comprising
   a porous or semi-porous matrix of collagen;
   at least one osteoinductive factor which is demineralized bone particles, Bone Morphogenetic Protein-2 (BMP-2), Bone Morphogenetic Protein-7 (BMP-7) or a combination thereof; and,
   at least one growth factor wherein the growth factor is present on or within the matrix and/or is present on or within the osteoinductive factor.

44. The composition of claim 43, wherein the osteoinductive factor is bone particles, and wherein a weight ratio of collagen to demineralized bone is 10% to 90% collagen and 90% to 10% demineralized bone particles.

45. An osteogenic composition having enhanced osteogenic potential, the composition comprising
   a porous or semi-porous matrix of collagen;
   at least one osteoinductive factor; and,
   a Transforming Growth Factor-Beta (TGF-β) present on or within the matrix or on or within the osteoinductive factor.

46. The composition of claim 45 wherein the porous or semi-porous matrix of collagen comprises the form of a sponge.

47. An osteogenic composition of claim 45, the composition comprising:
   a porous or semi-porous matrix of collagen in the form of a sponge, wherein the collagen matrix in sponge form is about 75 weight percent of the composition;
   an osteoinductive factor which is demineralized bone powder, wherein the demineralized bone powder is about 25 weight percent of the composition; and,
   a Transforming Growth Factor-Beta (TGF-β) is sorbed into or onto the matrix at a weight ratio of about 2.5 μg to 5 μg of TGF-β per 40 mg of sponge, whereby a combination of the matrix, the osteoinductive factor and the TGF-β add to 100 weight percent of the composition.

48. The composition of claim 45 wherein the porous or semi-porous matrix comprises human collagen.

49. The composition of claim 45 wherein the osteoinductive factor comprises a plurality of demineralized bone particles.

50. A method for preparing an osteogenic composition in accordance with claim 45, said method comprising:
   providing a porous or semi-porous matrix of human collagen;
   providing a plurality of demineralized bone particles, whereby the bone particles serve as an osteoinductive factor;

combining the matrix and the particles; and, sorbing Transforming Growth Factor-Beta-2 (TGF-β2) into or onto the matrix, or into or onto the particles, or into or onto a combination of matrix and particles.

51. The method of claim 50, wherein the sorbing step comprises sorbing an aqueous solution of Transforming Growth Factor-Beta-2 (TGF-β2), and the weight percent ratio of aqueous TGF-β2 to demineralized bone particles is in a range of about 1 weight unit aqueous TGF-β2 to 1 weight unit collagen, to about 1 weight unit aqueous TGF-β2 to 1,000,000 weight units collagen.

52. The composition of claim 45 wherein the Transforming Growth Factor-Beta (TGF-β) is Transforming Growth Factor-Beta-2 (TGF-β2).

53. The composition of claim 52, wherein the amount of the TGF-β2 is about 50 pg to 500 mg TGF-β2 per 40 mg of sponge.

54. The composition of claim 53, wherein the amount of the TGF-β2 sponge is about 5 ng to 100 mg TGF-β2 per 40 mg of sponge.

55. The composition of claim 54, wherein the amount of the TGF-β2 is about 50 ng to 5 mg TGF-β2 per 40 mg of sponge.

56. An improved osteogenic composition having enhanced osteogenic potential, the composition comprising:

a bone graft material of about 65 to about 95 weight percent of a porous or semi-porous matrix of reconstituted collagen; and about 35 to about 5 weight percent of an osteoinductive factor which is demineralized bone particles, solubilized bone morphogenetic protein, or mixtures of demineralized bone particles and solubilized bone morphogenetic protein; wherein the improvement comprises, at least one growth factor, nutrient factor, drug, calcium-containing compound, anti-inflammatory agent, blood product, calcium-containing compound, large molecular weight protein, or combination thereof is added to the composition.

* * * * *